United States Patent
Plojoux et al.

(10) Patent No.: US 9,693,587 B2
(45) Date of Patent: Jul. 4, 2017

(54) EXTRACTOR FOR AN AEROSOL-GENERATING DEVICE

(71) Applicant: Philip Morris Products S.A., Neuchatel (CH)

(72) Inventors: Julien Plojoux, Geneva (CH); Olivier Greim, Villars-Burquin (CH); Dani Ruscio, Cressier (CH)

(73) Assignee: Philip Morris Products S.A., Neuchatel (CH)

( * ) Notice: Subject to any disclaimer, the term of this patent is extended or adjusted under 35 U.S.C. 154(b) by 123 days.

(21) Appl. No.: 14/359,832

(22) PCT Filed: Nov. 20, 2012

(86) PCT No.: PCT/EP2012/073135
§ 371 (c)(1),
(2) Date: May 21, 2014

(87) PCT Pub. No.: WO2013/076098
PCT Pub. Date: May 30, 2013

(65) Prior Publication Data
US 2015/0013696 A1    Jan. 15, 2015

(30) Foreign Application Priority Data

Nov. 21, 2011  (EP) .................................... 11250907
Feb. 13, 2012  (EP) .................................... 12155245

(51) Int. Cl.
*A24F 47/00*  (2006.01)
*A61M 15/06*  (2006.01)

(52) U.S. Cl.
CPC .......... *A24F 47/008* (2013.01); *A24F 47/004* (2013.01); *A61M 15/06* (2013.01)

(58) Field of Classification Search
CPC .......... A61M 15/06; A24F 47/00; A24F 47/02; A24F 47/002; A24F 47/006; A24F 47/008
See application file for complete search history.

(56) References Cited

U.S. PATENT DOCUMENTS

| | | | |
|---|---|---|---|
| 5,144,962 | A | 9/1992 | Counts et al. |
| 5,240,012 | A | 8/1993 | Ehrman et al. |

(Continued)

FOREIGN PATENT DOCUMENTS

| | | |
|---|---|---|
| CN | 201079011 Y | 7/2008 |
| CN | 101500443 A | 8/2009 |

(Continued)

OTHER PUBLICATIONS

International Preliminary Report on Patentability and Written Opinion issued Jun. 5, 2014 in PCT/EP2012/073135.

(Continued)

*Primary Examiner* — Anthony Calandra
(74) *Attorney, Agent, or Firm* — Oblon, McClelland, Maier & Neustadt, L.L.P.

(57) ABSTRACT

There is provided an extractor for an aerosol-generating device configured to receive a smoking article including an aerosol-forming substrate and including a heater for heating the aerosol-forming substrate to form the aerosol. The extractor is configured to extract the smoking article received in the device, and includes a sliding receptacle configured to receive the smoking article, and a sleeve configured to receive the sliding receptacle. The sliding receptacle is slidable in the sleeve between a first position in which the substrate of the smoking article is positioned so as to be heated by the heater, and a second position in which the substrate is substantially separated from the heater. The sliding receptacle includes a support configured to support the substrate when the sliding receptacle and the smoking article are moved from the first position to the second (Continued)

position. There is also provided an electrically heated smoking system including the extractor.

14 Claims, 7 Drawing Sheets

(56) References Cited

U.S. PATENT DOCUMENTS

| | | | |
|---|---|---|---|
| 5,388,594 | A | 2/1995 | Counts et al. |
| 5,499,636 | A | 3/1996 | Baggett, Jr. et al. |
| 5,591,368 | A | 1/1997 | Fleischhauer et al. |
| 2006/0057106 | A1 | 3/2006 | Yamashita et al. |
| 2008/0021072 | A1 | 1/2008 | Luzenberg |
| 2008/0092912 | A1* | 4/2008 | Robinson ............ A24F 47/008 131/200 |
| 2009/0095311 | A1 | 4/2009 | Han |
| 2009/0126745 | A1 | 5/2009 | Hon |
| 2009/0223515 | A1 | 9/2009 | Watanabe |
| 2010/0024834 | A1 | 2/2010 | Oglesby et al. |
| 2010/0126505 | A1 | 5/2010 | Rinker |
| 2010/0313901 | A1 | 12/2010 | Fernando et al. |
| 2011/0209717 | A1 | 9/2011 | Han |
| 2011/0290269 | A1 | 12/2011 | Shimizu |
| 2012/0247494 | A1 | 10/2012 | Oglesby et al. |
| 2013/0014755 | A1* | 1/2013 | Kumar ................ A24F 47/006 128/202.21 |
| 2013/0125906 | A1 | 5/2013 | Hon |
| 2013/0139833 | A1 | 6/2013 | Hon |
| 2013/0276798 | A1 | 10/2013 | Hon |
| 2014/0305449 | A1* | 10/2014 | Plojoux ............... A24F 47/008 131/328 |

FOREIGN PATENT DOCUMENTS

| | | |
|---|---|---|
| CN | 101657116 A | 2/2010 |
| CN | 101862038 A | 10/2010 |
| EP | 2 022 349 | 2/2009 |
| EP | 2 394 520 A1 | 12/2011 |
| FR | 2 354 720 A1 | 1/1978 |
| GB | 741101 A | 11/1955 |
| GB | 2 469 850 | 11/2010 |
| GB | 2 473 264 | 3/2011 |
| WO | WO 94/06314 | 3/1994 |
| WO | WO 96/39879 | 12/1996 |
| WO | 2010 090338 | 8/2010 |

OTHER PUBLICATIONS

Extended European Search Report issued Oct. 5, 2012 in Patent Application No. 11250907.0.
Extended European Search Report issued Oct. 29, 2012 in Patent Application No. 12155245.9.
International Search Report Issued Feb. 6, 2014 in PCT/EP12/073135 Filed Nov. 20, 2012.
Written Opinion of the International Searching Authority Issued Feb. 6, 2014 in PCT/EP12/073135 Filed Nov. 20, 2012.
Office Action issued on Mar. 28, 2016 in Kazak Patent Application No. 2014/1618.1 (with English language translation).
English translation of Combined Chinese Office Action and Search Report issued on Nov. 4, 2015 in Patent Application No. 201280063987.0.
Notice of Opposition received in corresponding European Application No. 12805612.4, citing documents AA, AB, AO, and AP therein (37 pages).

* cited by examiner

EXTRACTOR FOR AN AEROSOL-GENERATING DEVICE

CROSS REFERENCE TO RELATED APPLICATION

This application is a national phase application based on PCT/EP2012/073135, filed on Nov. 20, 2012.

The present specification relates to an aerosol-generating device capable of positioning an aerosol-forming substrate therein. The specification further relates to an extractor for positioning an aerosol-forming substrate within the aerosol-generating device. The specification also relates to extracting a smoking article from an electrically heated smoking system.

A number of prior art documents disclose aerosol-generating devices that include, for example, heated smoking systems and electrically heated smoking systems. One advantage of these systems is that they significantly reduce sidestream smoke, while permitting the smoker to selectively suspend and reinitiate smoking. An example of a heated smoking system is disclosed in U.S. Pat. No. 5,144,962, which includes in one embodiment a flavour-generating medium in contact with a heater. When the medium is exhausted, both it and the heater are replaced. An aerosol-generating device where a substrate can be replaced without the need to remove the heating element is desirable.

The disclosure relates to an aerosol-generating device capable of positioning an aerosol-forming substrate, the device comprising a heater for heating the aerosol-forming substrate and configured for penetrating an internal portion of the aerosol-forming substrate and an extractor, wherein the extractor is capable of positioning the internal portion of the substrate in contact with the heater.

As used herein, the term 'positioning' relates to the movement of the aerosol-forming substrate relative to the heater of the aerosol-generating device. Thus, the extractor is capable of moving the aerosol-forming substrate relative to the heater in order to facilitate the removal of the aerosol-forming substrate from the aerosol-generating device.

As used herein, an 'aerosol-generating device' relates to a device that interacts with an aerosol-forming substrate to generate an aerosol. The aerosol-forming substrate may be part of an aerosol-generating article, for example part of a smoking article. An aerosol-generating device may comprise one or more components used to supply energy from a power supply to an aerosol-forming substrate to generate an aerosol. For example, an aerosol-generating device may be a heated aerosol-generating device. An aerosol-generating device may be an electrically heated aerosol-generating device or a gas-heated aerosol-generating device. An aerosol-generating device may be a smoking device that interacts with an aerosol-forming substrate of an aerosol-generating article to generate an aerosol that is directly inhalable into a user's lungs thorough the user's mouth. An aerosol-generating device may be a holder.

As used herein, the term 'aerosol-forming substrate' relates to a substrate capable of releasing volatile compounds that can form an aerosol. Such volatile compounds may be released by heating the aerosol-forming substrate. An aerosol-forming substrate may conveniently be part of an aerosol-generating article or smoking article.

As used herein, the terms 'aerosol-generating article' and 'smoking article' refer to an article comprising an aerosol-forming substrate that is capable of releasing volatile compounds that can form an aerosol. For example, an aerosol-generating article may be a smoking article that generates an aerosol that is directly inhalable into a user's lungs through the user's mouth. An aerosol-generating article may be disposable. The term 'smoking article' is generally used hereafter.

Preferably a smoking article is a heated smoking article, which is a smoking article comprising an aerosol-forming substrate that is intended to be heated rather than combusted in order to release volatile compounds that can form an aerosol. The aerosol formed by heating the aerosol-forming substrate may contain fewer known harmful constituents than would be produced by combustion or pyrolytic degradation of the aerosol-forming substrate. A smoking article may be, or may comprise, a tobacco stick.

In one embodiment, the extractor positions the aerosol-forming substrate in a first position and a second position, the first position being an operating position defined by the heater being in contact with the aerosol-forming substrate, and the second position being an extraction position defined by the aerosol-forming substrate being separated from the heater. Thus, the extractor may be movable coupled to an aerosol-generating device, and may be movable between a first position in which the aerosol-forming substrate is in contact with a heater of the aerosol-generating device, and a second position in which the aerosol-forming substrate is separated from the heater. Preferably the extractor remains coupled to the aerosol-generating device when in the first position, the second position and any intermediate point between the first position and second position. The extractor may be removably coupleable to the aerosol-generating device.

The extractor may comprise a sliding receptacle for receiving a smoking article, the sliding receptacle being slidable between the first position and the second position. The entire extractor including the sliding receptacle may move to translate the sliding receptacle between the first position and the second position. Alternatively, only the sliding receptacle of the extractor may be slidable between the first position and the second position.

The first position of the sliding receptacle is an operating position in which the heater can heat the aerosol-forming substrate of the smoking article to form the aerosol. As known to those of ordinary skill in the art, an aerosol is a suspension of solid particles or liquid droplets or both solid particles and liquid droplets in a gas, such as air. The second position of the sliding receptacle is an extraction position which facilitates removal of the smoking article from the aerosol-generating device. The upstream and downstream ends of the aerosol-generating device are defined with respect to the airflow when the user takes a puff. Typically, incoming air enters the aerosol-generating device at the upstream end, combines with the aerosol, and carries the aerosol in the airflow towards the user's mouth at the downstream end.

In one embodiment an aerosol-generating device is capable of receiving an aerosol-forming substrate. The device comprises a heater for heating the aerosol-forming substrate, the heater being configured for penetrating an internal portion of the aerosol-forming substrate, and an extractor for extracting the aerosol-forming substrate received in the aerosol-generating device. The extractor is movably coupled to the aerosol-generating device between a first position and a second position, the first position being an operating position defined by the heater being in contact with the aerosol-forming substrate, and the second position being an extraction position defined by the aerosol-forming substrate being separated from the heater.

The extractor may comprise a sliding receptacle for receiving the aerosol-generating article, an aperture being defined through a wall of the sliding receptacle for allowing the heater to penetrate the aerosol-forming substrate received within the sliding receptacle when the extractor is in the first position.

In one embodiment, a smoking article including the aerosol-forming substrate is provided to the aerosol-generating device. In this embodiment, the smoking article remains substantially stationary relative to the sliding receptacle as the sliding receptacle slides between the first position and the second position. The term "substantially stationary" is defined as a variation in position on the order of millimeters during use of the aerosol-generating device. The receptacle and the smoking article move relative to the other components of the aerosol-generating device, including the heater. This allows removal of the smoking article from the aerosol-generating device to be achieved in two phases. In a first phase, the smoking article and sliding receptacle are moved by sliding, while the aerosol-forming substrate is supported, relative to components of the aerosol-generating device, in particular the heater. In a second phase, the smoking article, now separate from the heater, can be removed from the sliding receptacle.

The invention allows the integrity of the aerosol-forming substrate to be substantially maintained as the smoking article is removed from the aerosol-generating device. The risk that loose shreds of aerosol-forming substrate are produced during removal and retained in the aerosol-generating device is significantly reduced. This is advantageous, for example, because the aerosol-generating device will need less frequent cleaning.

In one embodiment, the extractor further comprises a sleeve for receiving the sliding receptacle, such that the sliding receptacle is arranged to slide in the sleeve between the first and second positions. Alternatively, the sleeve may form part of the housing of the electrically heated smoking system and may not comprise a separate component.

The sleeve may comprise an open ended tube. The tube may be cylindrical. The sliding receptacle may comprise a cylindrical tube, or a substantially cylindrical shape, having a diameter slightly smaller than the diameter of the sleeve, such that the sliding receptacle can be received in the sleeve. The sliding receptacle may include a flange arranged to abut the sleeve when the sliding receptacle is in the first position. Assuming the smoking article is correctly received in the sliding receptacle, this allows the aerosol-forming substrate of the smoking article to be correctly positioned so as to be heated by the heater in the first position.

The aerosol-generating device may further comprise a stopper for preventing the sliding receptacle from sliding out of the aerosol-generating device when the sliding receptacle is moved to the second position. The stopper may be arranged to cooperate with stopper receiving means, for example an indent or depression for receiving the stopper. The stopper may be provided on the sliding receptacle. The stopper receiving means may be provided on the sleeve or on another part of the aerosol-generating device. Alternatively, the stopper may be provided on the sleeve or on another part of the aerosol-generating device and the stopper receiving means may be provided on the sliding receptacle.

The aerosol-generating device may further comprise a guide pin for guiding the sliding receptacle as the sliding receptacle is moved between the first and second positions. The guide pin substantially prevents the sliding receptacle from rotating in the aerosol-generating device or sleeve. The guide pin may be arranged to cooperate with a slot or groove. The guide pin, for example, may be provided on the sliding receptacle. The slot or groove may be provided in the sleeve or in another part of the aerosol-generating device. Alternatively, the guide pin may be provided on the sleeve or on another part of the aerosol-generating device and the slot or groove may be provided in the sliding receptacle.

The sliding receptacle may comprise insulating material, for providing insulation from the heat of the heater. Alternatively or additionally, the sleeve may comprise insulating material, for providing insulation from the heat of the heater.

The aerosol-generating device may be an electrically heated smoking system comprising an electric heater. In other embodiments the aerosol-generating device may be a heater smoking system comprising a gas-burner, or some source of heat other than electricity. In one embodiment, there is provided an electrically heated smoking system for receiving a smoking article including an aerosol-forming substrate, the electrically heated smoking system capable of positioning the aerosol-forming substrate and comprising: an electric heater for heating the aerosol-forming substrate and configured for penetrating an internal portion of the aerosol-forming substrate; and an extractor for extracting a smoking article received in the electrically heated smoking system, wherein the extractor is capable of positioning the internal portion of the aerosol-forming substrate in contact with the heater, the extractor comprising a sliding receptacle for receiving the smoking article, the sliding receptacle being slidable between a first position in which the aerosol-forming substrate of the smoking article is positioned so as to be heated by the electric heater, and a second position in which the aerosol-forming substrate is substantially separated from the electric heater.

The term "electric heater" refers to one or more electric heating elements. The electric heater may comprise an internal electric heating element for at least partially inserting into the aerosol-forming substrate of the smoking article when the smoking article is received in the sliding receptacle and the sliding receptacle is in the first position. An "internal heating element" is one which is suitable for insertion into an aerosol-forming material. The invention is particularly advantageous when used in conjunction with an internal heating element since, in that case, there may be a tendency for the aerosol-forming substrate to stick to the heating element and therefore to break up as the aerosol-forming substrate is separated from the heating element.

Alternatively or additionally, the electric heater may comprise an external heating element. The term "external heating element" refers to one that at least partially surrounds the aerosol-forming substrate. The electric heater may comprise one or more internal heating elements and one or more external heating elements.

The electric heater may comprise a single heating element. Alternatively, the electric heater may comprise more than one heating element. The heating element or heating elements may be arranged appropriately so as to most effectively heat the aerosol-forming substrate.

The electric heater may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physicochemical properties required. Alternatively, the electric heater may comprise an infra-red heating element, a photonic source, or an inductive heating element.

The electric heater may take any suitable form. For example, the electric heater may take the form of a heating blade. Alternatively, the electric heater may take the form of a casing or substrate having different electro-conductive portions, or an electrically resistive metallic tube. Alternatively, one or more heating needles or rods that run through the centre of the aerosol-forming substrate may be as already described. Alternatively, the electric heater may be a disk (end) heater or a combination of a disk heater with heating needles or rods. Other alternatives include a heating wire or filament, for example a Ni—Cr (Nickel-Chromium), platinum, tungsten or alloy wire or a heating plate. Optionally, the heating element may be deposited in or on a rigid carrier material.

The electric heater may comprise a heat sink, or heat reservoir comprising a material capable of absorbing and storing heat and subsequently releasing the heat over time to the aerosol-forming substrate. The heat sink may be formed of any suitable material, such as a suitable metal or ceramic material. In one embodiment, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, metal salt, a mixture of eutectic salts or an alloy.

The heat sink or heat reservoir may be arranged such that it is directly in contact with the aerosol-forming substrate and can transfer the stored heat directly to the substrate. Alternatively, the heat stored in the heat sink or heat reservoir may be transferred to the aerosol-forming substrate by means of a heat conductor, such as a metallic tube.

The electric heater may heat the aerosol-forming substrate by means of conduction. The electric heater may be at least partially in contact with the substrate, or the carrier on which the substrate is deposited. Alternatively, the heat from the electric heater may be conducted to the substrate by means of a heat conductive element.

Alternatively, the electric heater may transfer heat to the incoming ambient air that is drawn through the electrically heated smoking system during use, which in turn heats the aerosol-forming substrate by convection. The ambient air may be heated before passing through the aerosol-forming substrate.

In one embodiment, electric energy is supplied to the electric heater until the heating element or elements of the electric heater reach a temperature of between approximately 250° C. and 440° C. Any suitable temperature sensor and control circuitry may be used in order to control heating of the heating element or elements to reach the temperature of between approximately 250° C. and 440° C. This is in contrast to conventional cigarettes in which the combustion of tobacco and cigarette wrapper may reach 800° C.

The sliding receptacle may include a support for supporting the aerosol-forming substrate of the smoking article as the sliding receptacle and the smoking article are being moved from the first position to the second position.

In one embodiment, the support for supporting the aerosol-forming substrate of the smoking article comprises a face of the sliding receptacle, the face including at least one aperture for allowing through-flow of air. The size, shape and position of the aperture can be adapted to control or guide the air flow, for example the direction and amount of air flow. The air flow can be guided towards the vicinity of the heater, in order to improve the aerosol generation.

The face or surface of the sliding receptacle may provide the support which assists in maintaining the integrity of the aerosol-forming substrate, particularly as the sliding receptacle is moved from the first position to the second position. The size and shape of the at least one aperture may affect the air flowing through the aerosol-generating device. This may, in turn, affect the characteristics of the aerosol. Therefore, the at least one aperture may have a size and shape chosen according to the desired aerosol characteristics. This can improve air flow management and hence improve overall efficiency of the aerosol-generating device.

The size and shape of the at least one aperture may also be chosen depending on the properties of the aerosol-forming substrate. For example, if the aerosol-forming substrate comprises large pieces or shreds, a large aperture may be appropriate. However, if the aerosol-forming substrate comprises smaller pieces or shreds, a smaller aperture may be desired to prevent the small pieces falling through the aperture.

The at least one aperture may comprise one, two, three, four or a larger number of apertures. In an embodiment of the invention, the face of the sliding receptacle comprises a mesh or gauze. If the sliding receptacle comprises a cylindrical tube, the support may comprise an end face, or part of an end face, of the cylindrical tube.

One of the at least one apertures may be arranged for the heater to extend through the aperture when the sliding receptacle is in the first position.

In one embodiment, the sliding receptacle comprises gripping means for gripping the smoking article when the smoking article is received in the sliding receptacle and the sliding receptacle is in the first position.

The gripping means ensure that the smoking article is correctly positioned so that the heater can heat the aerosol-forming substrate of the smoking article when the user puffs. In addition, the gripping means ensure that the smoking article does not fall out of the aerosol-generating device if the smoking system is oriented away from the vertical or away from the operating orientation. The gripping means may be arranged to grip the smoking article when a smoking article is received in the sliding receptacle, whether the sliding receptacle is in the first position or in the second position. Alternatively, the gripping means may be arranged to grip the smoking article when a smoking article is received in the sliding receptacle only when the sliding receptacle is in the first position.

As mentioned above, removal of the smoking article from the aerosol-generating device may be achieved in two phases. In the first phase, the smoking article and sliding receptacle are moved, by sliding, relative to components of the aerosol-generating device. In one embodiment, the gripping means are arranged to grip the smoking article during the first phase. In the second phase, the smoking article, now separate from the heater, can be removed from the sliding receptacle. The gripping means may also be arranged to release the smoking article during the second phase.

The gripping means may be activated when the sliding receptacle is moved into the first position. Alternatively, the gripping means is activated only when a smoking article is received in the sliding receptacle. This is advantageous as it allows a user to insert a smoking article easily into the sliding receptacle, even when it is in the first position, without the user having to overcome any forces exerted by the gripping means. For example, the gripping means may comprise mechanical gripping means arranged to be in a non-gripping position when no smoking article is received in the sliding receptacle and arranged to move to a gripping position when a smoking article is received in the sliding receptacle. The gripping means may move from the non-gripping position to the gripping position by a force exerted by the smoking article itself.

The sliding receptacle may comprise a face against which the smoking article abuts when the aerosol-forming substrate of the smoking article is correctly positioned so as to be heated by the heater. This indicates to the user that the smoking article is fully inserted into the sliding receptacle. This reduces the chance of damage to the aerosol-forming substrate during insertion.

In one embodiment, the aerosol-generating device further comprises moving means for moving the sliding receptacle between the first and second positions.

The moving means may comprise motorised moving means. The sliding receptacle may be moved between the first and second positions automatically when the user exerts a force on the smoking article to remove the smoking article from the aerosol-generating device. Alternatively, the sliding receptacle may be moved between the first and second positions automatically when the user operates a switch. Alternatively, no moving means may be provided and the sliding receptacle may be moved between the first and second positions manually by a user.

During operation, the smoking article containing the aerosol-forming substrate may be completely contained within the aerosol-generating device. In that case, a user may puff on a mouthpiece of the aerosol-generating device. Alternatively, during operation the smoking article containing the aerosol-forming substrate may be partially contained within the aerosol-generating device. In that case, the user may puff directly on the smoking article.

The smoking article may be substantially cylindrical in shape. The smoking article may be substantially elongate. The smoking article may have a length and a circumference substantially perpendicular to the length. The aerosol-forming substrate may be substantially cylindrical in shape. The aerosol-forming substrate may be substantially elongate. The aerosol-forming substrate may also have a length and a circumference substantially perpendicular to the length. The aerosol-forming substrate may be received in the sliding receptacle of the aerosol-generating device such that the length of the aerosol-forming substrate is substantially parallel to the airflow direction in the aerosol-generating device.

The smoking article may have a total length between approximately 30 mm and approximately 100 mm. The smoking article may have an external diameter between approximately 5 mm and approximately 12 mm. The smoking article may comprise a filter plug. The filter plug may be located at the downstream end of the smoking article. The filter plug may be a cellulose acetate filter plug. The filter plug is approximately 7 mm in length in one embodiment, but may have a length of between approximately 5 mm to approximately 10 mm.

In one embodiment, the smoking article has a total length of approximately 45 mm. The smoking article may have an external diameter of approximately 7.2 mm. Further, the aerosol-forming substrate may have a length of approximately 10 mm. Alternatively, the aerosol-forming substrate may have a length of approximately 12 mm. Further, the diameter of the aerosol-forming substrate may be between approximately 5 mm and approximately 12 mm. The smoking article may comprise an outer paper wrapper. Further, the smoking article may comprise a separation between the aerosol-forming substrate and the filter plug. The separation may be approximately 18 mm, but may be in the range of approximately 5 mm to approximately 25 mm.

The aerosol-forming substrate may be a solid aerosol-forming substrate. Alternatively, the aerosol-forming substrate may comprise both solid and liquid components. The aerosol-forming substrate may comprise a tobacco-containing material containing volatile tobacco flavour compounds which are released from the substrate upon heating. Alternatively, the aerosol-forming substrate may comprise a non-tobacco material. The aerosol-forming substrate may further comprise an aerosol former. Examples of suitable aerosol formers are glycerine and propylene glycol.

If the aerosol-forming substrate is a solid aerosol-forming substrate, the solid aerosol-forming substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco and expanded tobacco. The solid aerosol-forming substrate may be in loose form, or may be provided in a suitable container or cartridge. Optionally, the solid aerosol-forming substrate may contain additional tobacco or non-tobacco volatile flavour compounds, to be released upon heating of the substrate. The solid aerosol-forming substrate may also contain capsules that, for example, include the additional tobacco or non-tobacco volatile flavour compounds and such capsules may melt during heating of the solid aerosol-forming substrate.

Optionally, the solid aerosol-forming substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix.

The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

Although reference is made to solid aerosol-forming substrates above, it will be clear to one of ordinary skill in the art that other forms of aerosol-forming substrate may be included in other embodiments of the invention. For example, the aerosol-forming substrate may be a liquid aerosol-forming substrate. If a liquid aerosol-forming substrate is provided, the aerosol-generating device preferably comprises means for retaining the liquid. For example, the liquid aerosol-forming substrate may be retained in a container. Alternatively or in addition, the liquid aerosol-forming substrate may be absorbed into a porous carrier material. The porous carrier material may be made from any suitable absorbent plug or body, for example, a foamed metal or plastics material, polypropylene, terylene, nylon fibres or ceramic. The liquid aerosol-forming substrate may be retained in the porous carrier material prior to use of the aerosol-generating device or alternatively, the liquid aerosol-forming substrate material may be released into the porous carrier material during, or immediately prior to use. For example, the liquid aerosol-forming substrate may be provided in a capsule. The shell of the capsule preferably melts upon heating and releases the liquid aerosol-forming substrate into the porous carrier material. The capsule may optionally contain a solid in combination with the liquid.

Alternatively, the carrier may be a non-woven fabric or fibre bundle into which tobacco components have been incorporated. The non-woven fabric or fibre bundle may comprise, for example, carbon fibres, natural cellulose fibres, or cellulose derivative fibres.

Where the aerosol-generating device is an electrically heated smoking system, the electrically heated smoking system may further comprise a power supply for supplying power to the electric heater. The power supply may be any suitable power supply, for example a DC voltage source. In one embodiment, the power supply is a Lithium-ion battery. Alternatively, the power supply may be a Nickel-metal hydride battery, a Nickel cadmium battery, or a Lithium based battery, for example a Lithium-Cobalt, a Lithium-Iron-Phosphate or a Lithium-Polymer battery.

The electrically heated smoking system may further comprise electronic circuitry arranged to be connected to the power supply and the electric heater. If more than one heating element is provided, the electronic circuitry may provide for the heating elements to be independently controllable. The electronic circuitry may be programmable.

In one embodiment, the aerosol-generating device further comprises a sensor to detect air flow indicative of a user taking a puff which enables puff based activation of the electric heater or an improved energy management of the electric heater. The sensor may be any of: a mechanical device, an electro-mechanical device, an optical device, an opto-mechanical device and a micro electro-mechanical systems (MEMS) based sensor. In that embodiment, the sensor may be connected to the power supply and the system is arranged to activate the electric heater when the sensor senses a user taking a puff. In an alternative embodiment, the system further comprises a manually operable switch, for a user to initiate a puff or to enable a long-lasting smoking experience.

The aerosol-generating device may further comprise a housing for receiving the smoking article containing the aerosol-forming substrate and designed to be grasped by a user. The aerosol-generating device may still further comprise an air inlet. The aerosol-generating device may still further comprise an air outlet. The aerosol-generating device may still further comprise a condensation chamber for allowing the aerosol having the desired characteristics to form.

According to a second aspect, there is provided an extractor for an aerosol-generating device, the aerosol-generating device for receiving a smoking article including an aerosol-forming substrate and comprising a heater for heating the aerosol-forming substrate to form the aerosol, the extractor for extracting a smoking article received in the aerosol-generating device and comprising: a sliding receptacle for receiving the smoking article; and a sleeve for receiving the sliding receptacle, wherein sliding receptacle is slidable in the sleeve between a first position in which the aerosol-forming substrate of the smoking article is positioned so as to be heated by the heater, and a second position in which the aerosol-forming substrate is substantially separated from the heater, the sliding receptacle including a support to support the aerosol-forming substrate of the smoking article as the sliding receptacle and the smoking article are being moved from the first position to the second position.

In one embodiment, there is provided an extractor for an electrically heated smoking system, the electrically heated smoking system for receiving a smoking article including an aerosol-forming substrate and comprising an electric heater for heating the aerosol-forming substrate to form the aerosol, the extractor for extracting a smoking article received in the electrically heated smoking system and comprising: a sliding receptacle for receiving the smoking article; and a sleeve for receiving the sliding receptacle; wherein the sliding receptacle is slidable in the sleeve between a first position in which the aerosol-forming substrate of the smoking article is positioned so as to be heated by the electric heater, and a second position in which the aerosol-forming substrate is substantially separated from the electric heater, the sliding receptacle including a support to support the aerosol-forming substrate of the smoking article as the sliding receptacle and the smoking article are being moved from the first position to the second position.

The extractor may further comprise a stopper for preventing the sliding receptacle from sliding out of the sleeve when the sliding receptacle is moved to the second position. The stopper may be provided on the sliding receptacle or on the sleeve. The stopper may be arranged to cooperate with stopper receiving means. The stopper receiving means may be provided on the sleeve or on the sliding receptacle.

The extractor may further comprise a guide pin for guiding the sliding receptacle in the sleeve as the sliding receptacle is moved between the first and second positions. The guide pin may be provided on the sliding receptacle or on the sleeve. The guide pin may be arranged to cooperate with a slot or groove. The slot or groove may be provided on the sleeve or on the sliding receptacle.

The sliding receptacle may comprise gripping means for gripping the smoking article when the smoking article is received in the sliding receptacle and the sliding receptacle is in the first position.

Other features described in relation to the aerosol-generating device and the aerosol-generating device may also be applicable to the extractor.

A further aspect may provide an aerosol-forming substrate extractor for removing an aerosol-forming substrate from an aerosol-generating device. The aerosol-forming substrate extractor is removably couplable to the aerosol-generating device and comprises a sliding receptacle for receiving the aerosol-forming substrate. An aperture is defined through a first wall of the receptacle such that the first wall is capable of engaging with the aerosol-forming substrate while allowing a heater of the aerosol-generating device to penetrate the receptacle and contact the aerosol-forming substrate.

The sliding receptacle may be, when coupled to the aerosol-generating device, slidable between a first position in which the aerosol-forming substrate is positioned so as to be heated by the heater, and a second position in which the aerosol-forming substrate is substantially separated from the heater.

The aerosol-forming substrate extractor, when coupled to the aerosol-generating device, may form part of the external housing of the aerosol-generating device. For example, the aerosol-generating device may comprise a housing that is formed from at least two separable portions, and the extractor may comprise one of those portions.

An aerosol-generating device according to any aspect or embodiment described above may comprise an extractor as described herein.

According to a third aspect, there is provided a method for extracting a smoking article including an aerosol-forming substrate from an aerosol-generating device, the aerosol-generating device comprising a heater for heating the aerosol-forming substrate to form the aerosol and an extractor comprising a sliding receptacle for receiving the smoking article, the method comprising: sliding the sliding receptacle, with a smoking article received in the sliding receptacle, from a first position in which the aerosol-forming substrate of the smoking article is positioned so as to be heated by the heater, to a second position in which the aerosol-forming substrate of the smoking article is substantially separated from the heater, the aerosol-forming substrate of the smoking article being supported during the sliding by a support on the sliding receptacle; and removing the smoking article from the sliding receptacle. Preferably, the extractor remains coupled to the device in both the first position and the second position.

In one embodiment, there is provided a method for extracting a smoking article including an aerosol-forming substrate from an electrically heated smoking system, the electrically heated smoking system comprising an electric heater for heating the aerosol-forming substrate to form the aerosol and an extractor comprising a sliding receptacle for receiving the smoking article, the method comprising: sliding the sliding receptacle, with a smoking article received in the sliding receptacle, from a first position in which the aerosol-forming substrate of the smoking article is positioned so as to be heated by the electric heater, to a second position in which the aerosol-forming substrate of the smoking article is substantially separated from the electric heater, the aerosol-forming substrate of the smoking article being supported during the sliding by a support on the sliding receptacle; and removing the smoking article from the sliding receptacle.

Features described in relation to one aspect of the invention may also be applicable to another aspect of the invention.

The invention will be further described, by way of example only, with reference to the accompanying drawings, in which.

Figure 1:
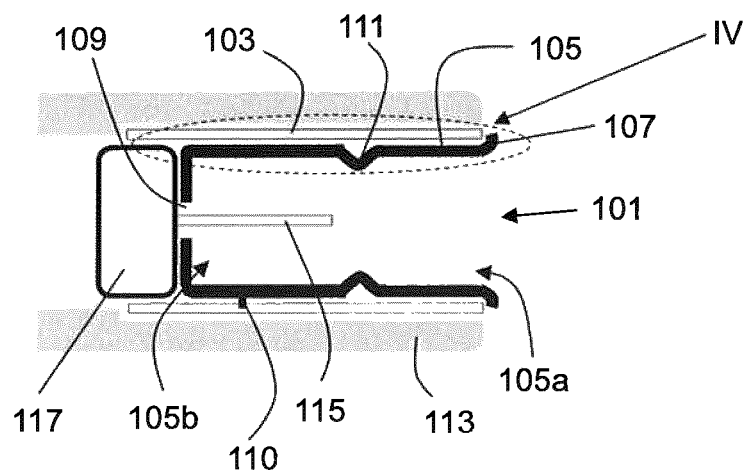
FIG. 1 is a schematic diagram of an extractor in an aerosol-generating device according to one embodiment of the invention.

FIG. 1 shows an aerosol-generating device 1 including an extractor 101 according to one embodiment of the invention. In this embodiment, the extractor 101 comprises a sleeve 103 and a sliding receptacle in the form of holder 105. In FIG. 1 the extractor 101 is shown in a first position, e.g., an operating position, without an aerosol-forming substrate. In this embodiment, the sleeve 103 comprises a substantially cylindrical tube. In this embodiment, the holder 105 also comprises a substantially cylindrical tube, but has a diameter slightly smaller than that of the sleeve 103, such that holder 105 can be slidably received in sleeve 103. The outer end 105a of the holder 105 is open to receive an aerosol-forming substrate and includes flange 107. In this embodiment, the flange 107 is in the form of a projecting rim or collar, which abuts against the outer end of sleeve 103 when the extractor is in the first, operating position. In this embodiment, the inner end 105b of the holder 105 is closed, except for an aperture 109. The holder 105 also includes a guide pin 110 which protrudes out of the holder 105 and into a slot or groove (not shown) in the inside wall of sleeve 103. The holder 105 also includes gripping means 111, to be described further below.

As shown in FIG. 1, in the first, operating position, the holder 105 is positioned completely within the sleeve 103, with the flange 107 at the outer end of the holder 105 abutting against the sleeve 103. The holder and sleeve are positioned within an aerosol-generating device housing 113, e.g., an electrically heated smoking system. In the first position shown in FIG. 1, the heater of the aerosol-generating device, which is in the form of heating element 115, extends through the aperture 109 in the inner end of the holder 105. The inner end 105b of the holder 105 is adjacent, and may abut the support 117 for the heating element 115.

Figure 2A:
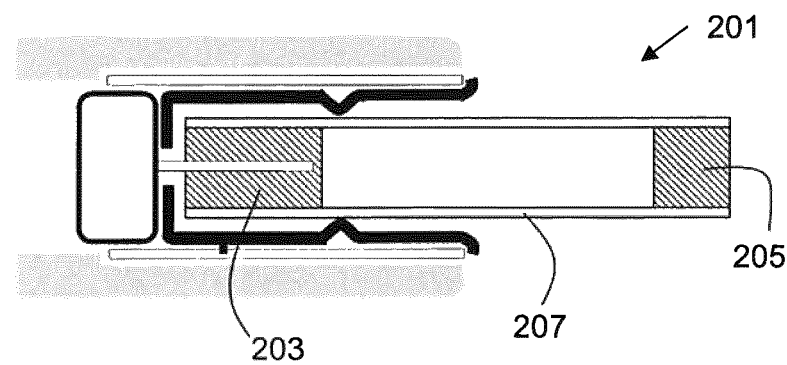
FIG. 2A is a schematic diagram of the extractor of FIG. 1 in a first position.

FIG. 2A shows the extractor 101 of FIG. 1, with a smoking article 201 inserted into the aerosol-generating device. The reference numerals for the extractor are not shown in FIG. 2 for simplicity. In this embodiment, the smoking article 201 has an elongate cylindrical shape and comprises an aerosol-forming substrate 203, and a filter plug 205, arranged sequentially and in coaxial alignment. The aerosol-forming substrate 203 and filter plug 205 are overwrapped with an outer paper wrapper 207. Other components may be included in the smoking article.

Figure 2B:
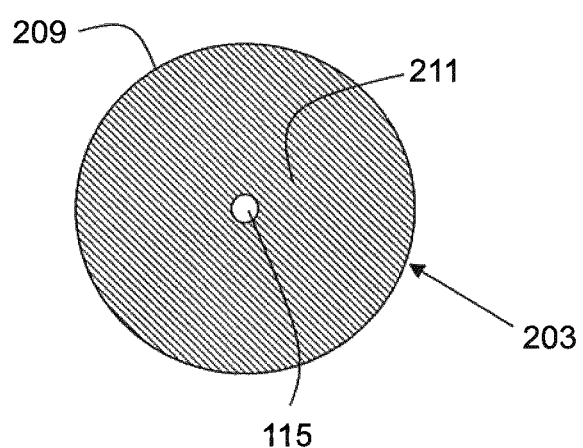
FIG. 2B is a schematic cross-sectional diagram of the extractor of FIG. 2A.

FIG. 2B shows a cross-section of the smoking article 201 illustrated in FIG. 2A. The aerosol-forming substrate 203 of the smoking article 201 is bounded by a circumference 209. Circumference 209 defines an internal portion 211 of the aerosol-forming substrate 203. When the extractor 101 is positioned in the first position, heating element 115 is provided in the internal portion of substrate 203 as illustrated in FIGS. 2A and 2B.

The first position of the holder 105 (shown in 2A) is an operating position, in which the heater can heat the aerosol-forming substrate 203 of the smoking article 201 to form the aerosol. As shown in FIG. 2A, in the first position, the smoking article 201, which is received in the holder 105, abuts against the inner end 105a of the holder 105. The gripping means 111 apply a force on the smoking article 201 to retain the smoking article 201 in position. The substantially closed inner end 105b of the holder 105 acts as a support for the aerosol-forming substrate 203 of the smoking article 201. The holder 105 is completely received within sleeve 103, with the flange 107 abutting the sleeve 103 and with the inner end 105b of the holder 105 adjacent, and may abut, the support 117 for the heating element 115 of the aerosol-generating device. The heating element 115 extends through aperture 109 in the inner end 105b of the holder 105 and into the aerosol-forming substrate 203 of the smoking article 201.

When a user puffs on the smoking article, air flows in the direction from the upstream end (the left side of FIG. 2) towards the downstream end (the right side of FIG. 2). Alternatively or additionally, air may flow from the right side, entering in the space between the housing 113 and the sleeve 103 or in the space between the sleeve 103 and the holder 105, passing to the left and then entering the inner end 105b through aperture 109. As the user puffs, the heating element 115 heats the aerosol-forming substrate 203 to create the aerosol. The aerosol is then carried in the air flow into the mouth of the user. Because the air flows through and adjacent to the aerosol-forming substrate, the air flows through aperture 109 in the inner end 105b of the holder 105. Thus, the size and shape of the aperture 109 can be used to manage the air flow and consequently the characteristics of the aerosol.

Figure 3:
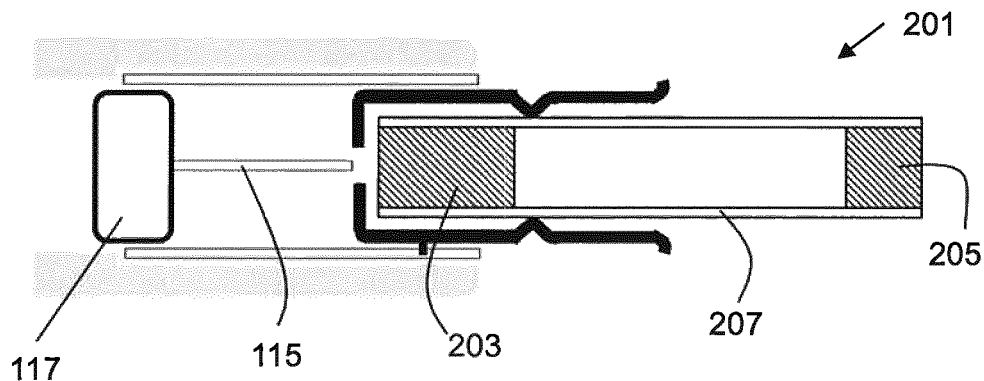
FIG. 3 is a schematic diagram of the extractor of FIG. 1 in a second position.

FIG. 3 shows the extractor and smoking article of FIG. 2A, when the holder 105 is in a second position, e.g., an extraction position. When the smoking article 201 is fully consumed, or the user considers the smoking article to be completely used up, the holder 105 may be moved from the first, operating position shown in FIG. 2A, to the second, extraction position shown in FIG. 3. As the holder is moved from the first, operating position to the second, extraction position, the guide pin 110 moves along the slot or groove (not shown) in the inside wall of the sleeve 103. This ensures that the holder does not rotate in the sleeve. The second position of the sliding receptacle is an extraction position which facilitates removal of the smoking article from the aerosol-generating device. As shown in FIG. 3, in the second, extraction position, the smoking article 201 is still received in the holder 105 and still abuts against the inner end 105a of the holder 105. However, the holder is now only partially received in the sleeve 103. The gripping means 111 still apply a force on the smoking article but the force is small because the holder 105 is not contained by the sleeve. The holder and smoking article are moved away from the heating element 115 so that heating element 115 no longer extends through aperture 109 or into the aerosol-forming substrate 203. A stopper on the holder (not shown in FIG. 3, to be described further with reference to FIG. 4) is provided to prevent the holder falling out of the sleeve.

As the holder is moved from the first, operating position into the second, extraction position shown in FIG. 3, the substantially closed inner end 105b of the holder 105 acts as a support for the aerosol-forming substrate 203 of the smoking article 201. Once the aerosol-forming substrate has been heated by the heating element 115, there is often a tendency for the heating element 115 to stick to the aerosol-forming substrate. This can lead to the break up of the aerosol-forming substrate as the smoking article is removed from the aerosol-generating device. However, in the embodiment illustrated in FIGS. 1 to 3, the substantially closed inner end of the holder 105 exerts a force on the aerosol-forming substrate as the holder is moved from the first, operating position to the second, extraction position, which counteracts any tendency of the aerosol-forming substrate to remain attached to the heating element and therefore disintegrate.

Figure 4:
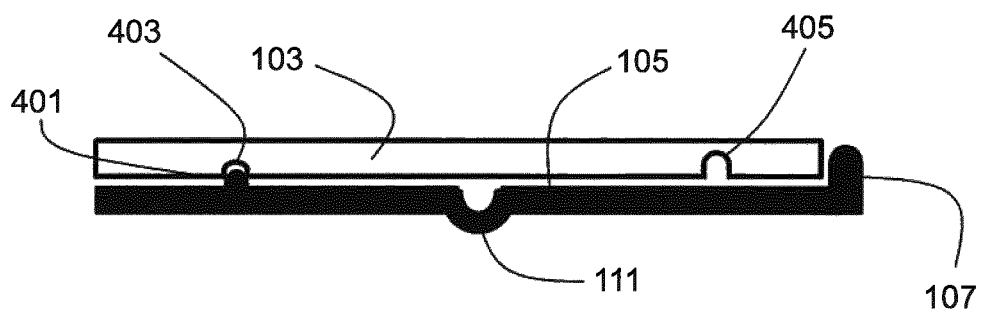
FIG. 4 is an enlarged schematic view of a portion of the extractor of FIG. 1.

FIG. 4 is an enlarged view of portion IV of FIG. 1. FIG. 4 shows a portion of the holder 105 inside the sleeve 103 in the first, operating position shown in FIG. 1. As can be seen in FIG. 4, the holder 105 includes a stopper 401 protruding from the outside of the holder. The sleeve includes two indents 403, 405 which are arranged to cooperate with stopper 401. When the holder is in the first, operating position (as shown in FIG. 4), stopper 401 is positioned in indent 403. When the holder is moved from the first, operating position, the curved shape of the stopper 401 and indent 403 allows stopper 401 to slide out of the indent 403. When the holder is in the second, extraction position (not shown in FIG. 4), stopper 401 is positioned in indent 405. The cooperation of the stopper 401 with indent 403 keeps the holder in the first, operating position. The cooperation of the stopper 401 with indent 405 keeps the holder in the second, extraction position. Indent 405 may be deeper than indent 403. This allows the stopper to be removed from indent 403 when the holder is moved from the first, operating position to the second, extraction position. However, this does not allow the holder to be extracted fully out of the sleeve. In one embodiment, the inner side of indent 405 may be more gradually sloped than outer side of indent 405. This allows the holder 105 to be moved from the second, extraction position back to the first, operating position.

In FIGS. 1 to 4, the stopper 401 and guide pin 110 are shown on opposite sides of the holder 105. However, the stopper 401 and guide pin 110 could be on the same side of the holder 105. In addition, the guide pin 110 may also assist with preventing the holder from falling out of the sleeve. For example, the guide pin may be arranged to abut one end of the slot or groove on the inside wall of the sleeve when the holder is in the second extraction position.

The sleeve 103 has a number of functions. Firstly, it guides the holder 105 as the holder 105 slides between the first, operating position and the second, extraction position. The sleeve 103 remains stationary with respect to the aerosol-generating device. The position of the flange 107 of the holder 105 against the sleeve 103 also positions the holder correctly relative to the heating element, so that when a smoking article is received in the holder, the heating element can heat the aerosol-forming substrate. Cooperation of the slot or groove in the sleeve with the guide pin 110 on the holder prevents rotation of the holder 105. In addition, the sleeve 103 can act to insulate the outer housing of the aerosol-generating device from the heating element 115. This is advantageous to prevent the outer housing of the aerosol-generating device becoming too hot to be safely held by a user. Although the sleeve is shown as a separate component in FIGS. 1 to 4, it is possible for the sleeve to be formed integrally with the aerosol-generating device itself.

The holder 105 has a number of functions. Firstly, it holds the smoking article and ensures it is correctly positioned for the heating element to heat the aerosol-forming substrate. In addition, the inner end of the holder supports the aerosol-forming substrate, particularly during the extraction process. This allows the integrity of the aerosol-forming substrate to be substantially maintained as the smoking article is extracted from the aerosol-generating device. Cooperation of the guide pin 110 on the holder with the slot or groove in the sleeve 103 prevents rotation of the holder 105 in the sleeve 103. In addition, the holder 105 can act to insulate the sleeve 103 from the heating element 115. Finally, the structure of the inner end of the holder 105, particularly the aperture 109, can be used to manage the air flow. This can affect the characteristics of the aerosol and can increase the efficiency of the aerosol-generating device.

In the embodiment described above with reference to FIGS. 1 to 4, the smoking article is in the form of an elongate cylindrical smoking article, including an aerosol-forming substrate 203 and a filter plug 205, arranged sequentially and in coaxial alignment and overwrapped by paper wrapper 207. The length of the elongate smoking article is parallel to the direction of airflow (not shown) when the user puffs on the smoking article. However, the smoking article need not have the form shown in FIGS. 1 to 4. For example, the smoking article may include additional components. The smoking article simply requires an aerosol-forming substrate which can be positioned so as to be heated by the heater when the smoking article is received in the holder of the extractor, and the extractor is in the first, operating position.

In the embodiment described above with reference to FIGS. 1 to 4, the heating element is in the form of an internal heating element. That is to say, the heating element 115 is arranged to be at least partially inserted into the aerosol-forming substrate of the smoking article when the extractor is in the first, operating position. In FIGS. 1 to 4, the heating element 115 is in the form of an elongate pin or rod of electrically resistive material. However, this is not necessarily the case and the heating element may have any appropriate form. However, it has been found that the extractor according to the invention is particularly advantageous when used in conjunction with an internal heating element. It has been found that maintaining the integrity of the aerosol-forming substrate during extraction of a smoking article from an aerosol-generating device having an internal heating element can be difficult. There is a tendency for the aerosol-forming substrate to stick to the heating element, which may be particularly troublesome when the heating element is an internal heating element. The extraction can result in some disintegration of the aerosol-forming substrate and loose shreds of the aerosol-forming substrate may remain in the system. The extractor of the invention reduces disintegration of the aerosol-forming substrate as the smoking article is being extracted from the aerosol-generating device, particularly when the aerosol-generating device includes an internal electric heating element which is at least partially inserted into the aerosol-forming substrate during heating. In the embodiment illustrated in FIGS. 1 to 4, the inner end 105b of the holder 105 is closed except for aperture 109. The aperture 109 allows the heating element 115 to extend through the inner end 105b of the holder 105 and into the aerosol-forming substrate. The aperture may have any suitable size which is smaller than the diameter of the holder. The inner end of the holder must be sufficient closed so that the inner end can provide some support to the aerosol-forming substrate, particularly as the smoking article is being removed from the aerosol-generating device. That is to say, the inner end of the holder has two functions. Firstly, the inner end of the holder acts as a support for the aerosol-forming substrate, particularly during the process of extracting the smoking article from the aerosol-generating device. This reduces the likelihood that the aerosol-forming substrate will break up or crumble. Secondly, the inner end of the holder allows air to flow from the upstream end of the aerosol-generating device through the aerosol-forming substrate during the heating process so that aerosol can be carried in the air flow into the user's mouth. In the case of an internal heating element, as shown in FIGS. 1 to 3, the inner end of the holder must also allow the heating element to extend through the inner end of the holder and into the aerosol-forming substrate.

The inner end may have any suitable alternative structure, however. The inner end of the holder may have a structure which is particularly suited to the type of aerosol-forming substrate. For example, the inner end of the holder may be perforated with a plurality of small holes. This will allow air to flow through the inner end of the holder. If a single internal heating element is used, the heating element can extend through one of the small holes. If a plurality of internal heating elements is used, the heating elements can extend through the small holes. Alternatively, the inner end may comprise gauze or mesh or another material that will allow air to flow through. The aperture in the inner end of the holder through which heating element or elements extends may be any suitable shape. For example, the aperture may be rectangular or circular. The shape of the aperture may be the same as the cross sectional shape of the heating element or elements.

As described in relation to FIG. 2, when the holder is in the first, operating position, the inner end of the holder is close to the support 117 for the heating element. By minimising the space between the inner end of the holder and the adjacent component, there is little space remaining for loose shreds of aerosol-forming substrate to be retained in the aerosol-generating device after the smoking article has been removed. Thus, the inner end of the holder can be designed to substantially fill the empty space between the adjacent component and the holder with just sufficient space for air to flow in.

As already mentioned, when a user is puffing on the smoking article in the aerosol-generating device, the holder 105 and smoking article 201 are in the first, operating position (shown in FIG. 2). The heating element 115 heats the aerosol-forming substrate 203 when the user puffs, to form the aerosol. Alternatively, the heating element 115 can heat continuously after an initial activation, for example triggered by a first puff of the user or by a switch activated by the user. The aerosol is carried in the air flow into the mouth of the user. When the smoking article is fully consumed, or the user considers the smoking article to be used up, the holder 105 can be moved from the first, operating position into the second, extraction position (shown in FIG. 3). This may be achieved manually by the user pulling the holder 105 out of the sleeve 103. In that case, the user may grip the flange 107 to pull the holder 105 out of the sleeve 103. Alternatively, this may be achieved automatically. For example, the user may activate a switch which activates a motor to slide the holder from the first, operating position to the second, extraction position. Alternatively, the automatic movement of the holder from the first, operating position to the second, extraction position may be activated by the user exerting a force on the smoking article to pull the smoking article out of the holder. The extractor may be returned to the first, operating position, for another smoking article, either manually or automatically. Alternatively, flange 107 may be connected to an outer shell (not shown) that conveys force and movement through flange 107 to operate holder 105 in the manners discussed above.

In the embodiment illustrated in FIGS. 1 to 4, holder 105 includes gripping means 111 for gripping the smoking article 201 when the holder 105 and smoking article 201 are in the first, operating position. In FIGS. 1 to 4, the gripping means have a relatively simply construction. The gripping means comprise a reduced diameter collar in the holder 105. When the holder is in the second, extraction position, the holder 105 is not contained within the sleeve 103. This allows the holder to expand very slightly which increases the diameter of the holder at the position of the gripping means 111. This allows a user to insert a smoking article into the holder, when the holder is in the second, extraction position. When the holder slides in the sleeve into the first, operating position, the holder diameter decreases slightly as it is slidably received in the sleeve. This allows the gripping means 111 to grip the smoking article and retain the smoking article in the correct position.

The gripping means, however, may have any suitable structure. In the case of automatic extraction of the holder from the sleeve, it is particularly important that the gripping means is activated at the appropriate time. In the embodiment illustrated in FIGS. 1 to 4, the gripping means 111 is activated when the holder 105 is moved into the first, operating position. Other embodiments of the gripping means may also be activated when the holder 105 is moved into the first, operating position. However, it is possible for a user to insert a smoking article into the holder 105 when the holder is already in the first, operating position. Thus, it would be advantageous for the gripping means to be activated only when a smoking article is received in the holder.

Figure 5:
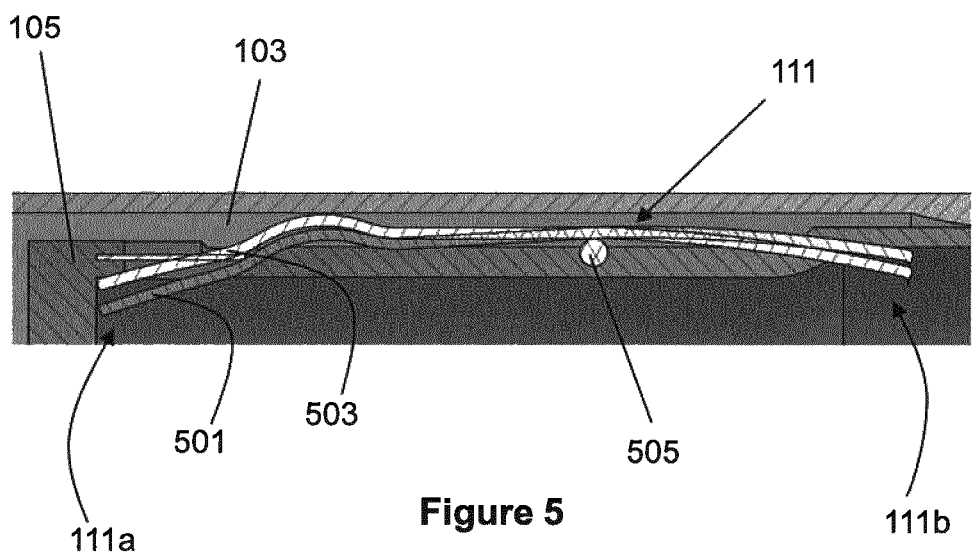
FIG. 5 is a schematic diagram of gripping means of an extractor according to one embodiment of the invention.

FIG. 5 shows one embodiment of gripping means which are activated when a smoking article is received in the holder. FIG. 5 is an enlarged view of one end of the holder 105 when it is contained in the sleeve 103 and in the first, operating position. Gripping means 111 have an inner end 111a nearest the inner end of the holder 105 and an outer end nearest the outer end of holder 105. Two positions 501, 503 are shown for gripping means 111. When no smoking article is received in the holder 105, the gripping means are positioned at position 501. That is to say, gripping means is biased to position 501 when no smoking article is in the holder 105. When a smoking article is inserted into the holder 105 and approaches the inner end of the holder 105, the smoking article presses against the inner end 111a of the gripping means 111. As a result, the gripping means 111 rotates around pivot 505 and moves into position 503. In position 503, the outer end 111b of the gripping means presses onto the smoking article so as to grip the smoking article and retain it in position in the holder 105. When the smoking article is to be removed from the holder 105, when a user pulls on the smoking article, as the smoking article moves just a short distance from the inner end of the holder, this releases the gripping means 111 and the gripping means 111 can rotate around pivot 505 back into position 501. In position 501, the outer end 111b of the gripping means moves outward and thus away from the smoking article so as release the smoking article.

Figure 6:
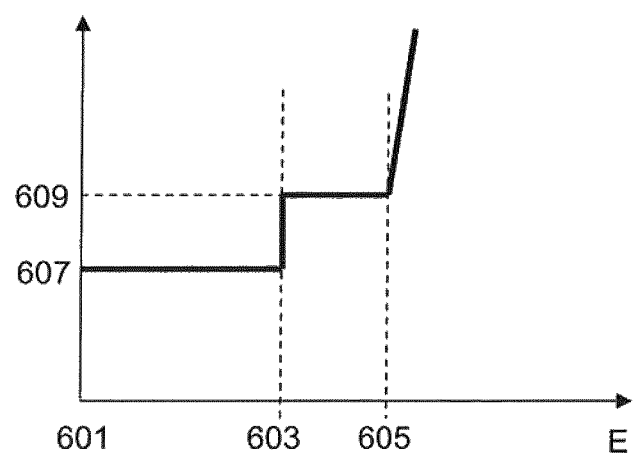
FIG. 6 is a schematic diagram illustrating the force to be applied on the smoking article including an aerosol-forming substrate for inserting or extracting the smoking article, depending upon the smoking article's position in the extractor.

FIG. 6 is a schematic diagram illustrating the force to be applied on the smoking article for inserting or extracting the smoking article, depending upon the smoking article's position in the extractor. The x-axis shows the position (E) of the smoking article in the extractor. The y-axis shows the force (F) required to insert the smoking article into the aerosol-generating device or to extract the smoking article from the aerosol-generating device. Between position 601 and 603, the smoking article is sliding within the holder 105. A force 607 is required to overcome the frictional force of the holder. Between position 603 and 605, the heating element 115 is being inserted into the smoking article aerosol-forming substrate. A force 609 is required to overcome the frictional force of the heating element 115 in addition to the frictional force of the holder 105. At position 605, the smoking article makes contact with the bottom 105b of the holder 105. The sudden increase in required force indicates to the user that the smoking article is in contact with the bottom of the holder and is in the correct position for the aerosol-forming substrate to be heated by the heating element.

Thus, the aerosol-generating device and extractor of the invention provide a straightforward means to remove the smoking article while minimising disintegration and break up of the aerosol-forming substrate. This is particularly advantageous when the heater comprise an internal heating element. The extractor may also be used to assist with airflow management in the aerosol-generating device.

Figure 7A:
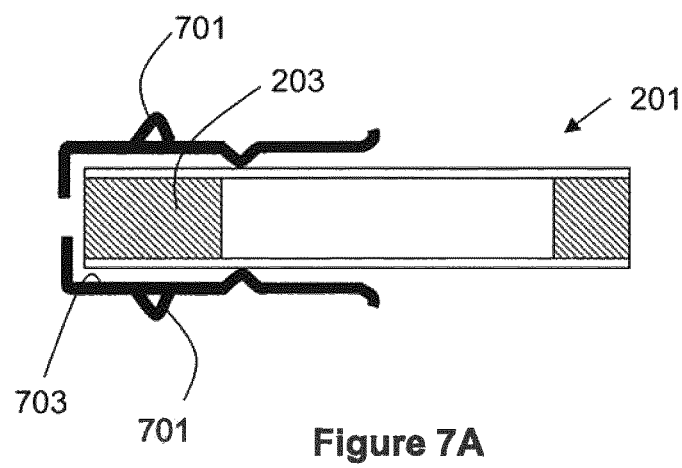
FIG. 7A is a schematic diagram of an extractor according to another embodiment of the invention.
Figure 7B:
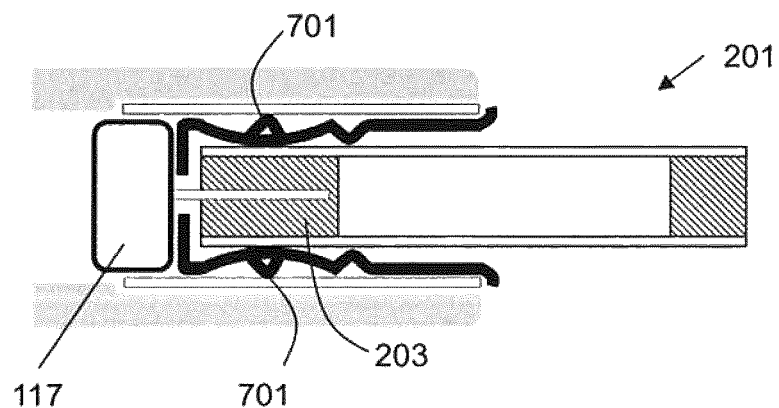
FIG. 7B is a schematic diagram of the extractor of FIG. 7A in a first position.

FIGS. 7A and 7B illustrate another embodiment of the extractor 101. In the embodiment illustrated in FIG. 7A, protuberances 701 are provided on the circumference of extractor 101. The protuberances 701 are positioned such that when the extractor 101 is provided in the operating position, the protuberances 701 cause a deflection of an inner wall 703 of the extractor 101. This deflection compresses the aerosol-forming substrate 203 of the smoking article 201.

Compression of the aerosol-forming substrate 203 may be desirable under certain circumstances. For example, compression of the aerosol-forming substrate 203 may improve the physical contact between the aerosol-forming substrate 203 and the heater. Moreover, compression of the aerosol-forming substrate 203 also effectively decreases the porosity of the aerosol-forming substrate 203. Here, porosity is defined as a ratio of air with respect to the substance forming the aerosol-forming substrate 203. For example, a higher percentage of air in a cross-sectional volume of the aerosol-forming substrate 203 corresponds to a higher porosity and a lower percentage of air corresponds to a lower porosity. In other words, as compression of the substance increases and air is forced out of the substance, the porosity decreases. As porosity decreases, the mean distance between portions of the substance forming the aerosol-forming substrate 203 also decreases and the substance becomes more dense.

Compression of the aerosol-forming substrate 203 may provide several beneficial effects, such as improved thermal conductivity and a more homogeneous temperature profile of the aerosol-forming substrate 203. With the improved thermal conductivity and more homogeneous profile of the aerosol-forming substrate 203, the percentage of undesirable elements in the aerosol can be even better controlled because a lower operating temperature can be used to produce an equivalent or greater amount of aerosol when compression of the aerosol-forming substrate 203 is used.

Although the protuberances 701 are illustrated as discrete points located opposite from each other in FIG. 7, it will be apparent to one of ordinary skill in the art that other configurations providing compression of the aerosol-forming substrate 203 may be used. For example, a single protuberance, multiple protuberances located opposite from each other axially, or protruding bands extending around the circumference of the smoking article 201 that allow for the compression of the aerosol-forming substrate 203 may be used. Alternatively, other configurations and distributions of protuberances with or without protruding bands may be used to create a desired compressive effect on the aerosol-forming substrate 203.

Figure 8A:
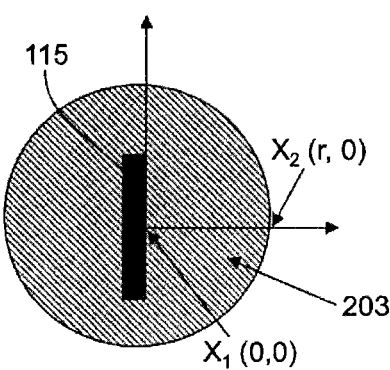
FIGS. 8A and 8B are schematic diagrams illustrating the thermal profile of a compressed aerosol-forming substrate and uncompressed aerosol-forming substrate.
Figure 8B:
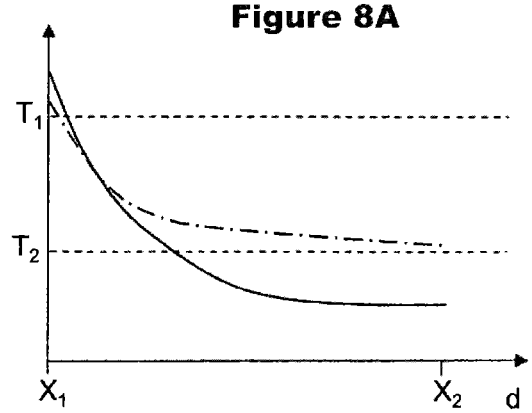

FIG. 8B illustrates the thermal profile of a compressed and uncompressed aerosol-forming substrate 203. FIG. 8A includes an illustration of an exemplary heating element 115, being formed in the shape of a blade, provided along the centre axis of the aerosol-forming substrate 203. The radius of the aerosol-forming substrate 203 is defined by a centre point ($X_1$) and a point on the perimeter of the aerosol-forming substrate 203 ($X_2$), where the radius has a length r. FIG. 8B shows exemplary thermal profiles with distance measured from the centre of exemplary aerosol-forming substrates 203 to the outer circumference of the same, i.e., the thermal profile on the radial line between $X_1$ and $X_2$. Temperature 1 ($T_1$) is a temperature above which undesirable components are released from the aerosol-forming substrate 203 or a maximum operating temperature. Temperature 2 ($T_2$) is the desired operating temperature that provides sufficient aerosol for operation. When heating the aerosol-forming substrate 203, a higher volume of aerosol can be formed if a larger percentage of the aerosol-forming substrate 203 is at a temperature above $T_2$.

As shown in FIG. 8B, the exemplary thermal profile of an uncompressed aerosol-forming substrate (shown by a solid line in FIG. 8B) is less desirable because the temperature falls more rapidly radically outward from the centre of the aerosol-forming substrate. In contrast, the compressed aerosol-forming substrate has a smoother exemplary thermal profile (shown by a broken line in FIG. 8B) and falls more slowly from the centre of the aerosol-forming substrate to the perimeter of the same. The compressed aerosol-forming substrate's lower porosity yields the improved thermal conductivity and more homogeneous temperature profile. Thus, the compressed aerosol-forming substrate yields a higher overall aerosol production without the need for higher operating temperature.

Figure 9A:
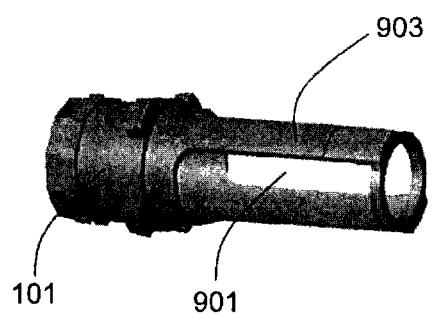
FIG. 9A is a schematic diagram of an extractor having windows according to a further embodiment of the invention.

FIG. 9A illustrates another embodiment of an extractor 101. As shown in FIG. 9A, windows 901 are provided in the extractor 101. The structural integrity of the extractor 101 including the windows 901 can be improved by using legs 903.

Figure 9B:
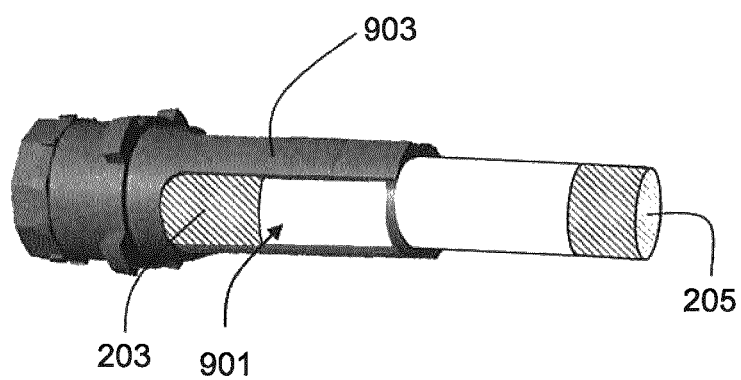
FIG. 9B is an illustration of the extractor of FIG. 9A with a smoking article received therein.

FIG. 9B illustrates the extractor 101 with windows 901 of FIG. 9A with a smoking article 201 received therein. In FIG. 9B, the outer paper wrapper 207 of the smoking article 201 is not shown so that the aerosol-forming substrate 203 and filter plug 205 of the smoking article 201 are visible. As shown in FIG. 9B, the windows 901 in the extractor 101 are provided over at least a part of the circumference 209 of the aerosol-forming substrate 203.

Use of windows 901 reduces surface contact between the extractor 101 and the smoking article 201. The windows 901 also reduce the thermal mass of the extractor 101. The reduction of surface contact and thermal mass reduces heat losses of the aerosol-forming substrate 203 and improves efficiency of the heating of the aerosol-forming substrate 203. This allows for higher levels of deliverables in the aerosol generated from the aerosol-forming substrate 203. The reduction of surface contact and thermal mass allows for a similar heat profile within the aerosol-forming substrate 203 as the exemplary one for the compressed aerosol-forming substrate illustrated in FIG. 8B.

The size of the windows 901 may be varied. So long as the extractor 101 maintains its structural integrity during operation, any combination of the windows 901 and the legs 903 may be used with the extractor 101. As will be apparent to one of ordinary skill in the art, increasing the size of windows 901 will reduce the surface contact and thermal mass of the extractor 101, thus improving the homogeneity of the thermal profile of the aerosol-forming substrate 203 and allowing for higher aerosol delivery levels. At a minimum, the lengths of the windows 901 are no smaller than the length of the aerosol-forming substrate 203 measured along a central axis of the smoking article 201.

The exemplary embodiments described above illustrate but do not limit the invention. In view of the above discussed exemplary embodiments, other embodiments consistent with the above discussed exemplary embodiments will now be apparent to one of ordinary skill in the art.

Figure 10:
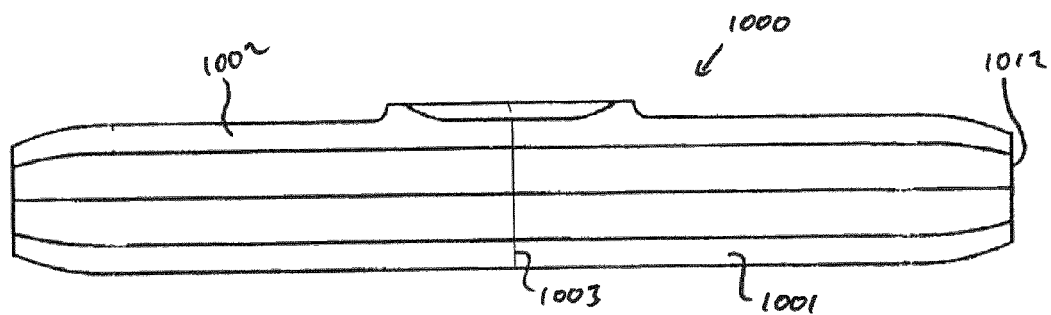
FIG. 10 is a schematic diagram illustrating an aerosol-generating device according to one embodiment of the invention.
Figure 11:
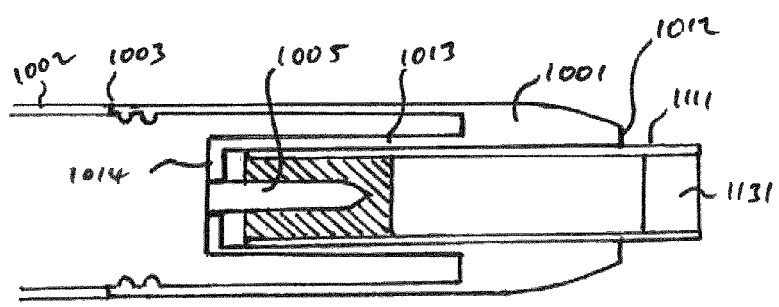
FIG. 11 is a schematic cross-sectional illustration of the device of FIG. 10 with a smoking article received therein.
Figure 12:
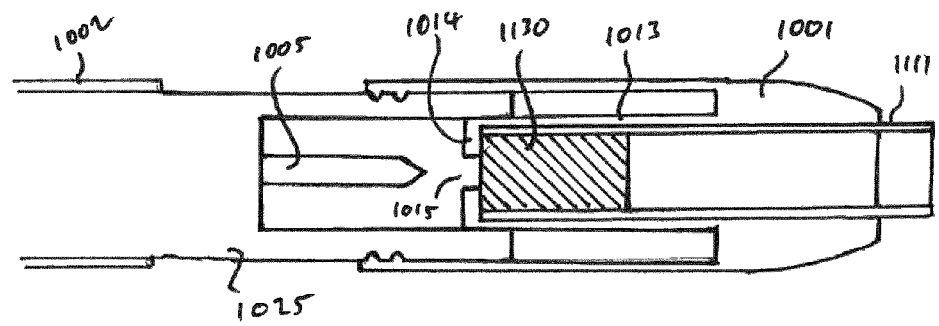
FIG. 12 is a schematic cross-sectional illustration of the device of FIG. 10 showing a smoking article being extracted.

FIGS. 10 to 12 illustrate a further specific embodiment of an aerosol-generating device 1000 having an extractor 1001 for positioning or extracting a smoking article 1111 that is received within the device 1000.

As can be seen from FIG. 10, the device 1000 has an elongated shape. The device has two external housing portions 1001, 1002 that are slidably separable at a join line 1003. A first housing portion 1002 is fixed relative to internal components of the device such as a battery (not shown) and a heater 1005. The heater 1005 is preferably an electrically heated spike, pin, or blade. A second housing portion 1001 forms the extractor.

The extractor 1001 comprises a sliding receptacle 1013 for receiving a smoking article 1111. The sliding receptacle 1013 defines an elongated substantially tubular cavity, opening at a first end 1012 of the device 1000 and dimensioned to receive a rod-shaped smoking article 1111 comprising an aerosol-forming substrate 1130. It is preferred that the aerosol-forming substrate is formed from a homogenised tobacco material. A distal end of the sliding receptacle, at an opposite end to its opening, is defined by an end wall 1014. The end wall is capable of engaging with the smoking article 1111. An aperture 1015 defined through the end wall 1014 is positioned and dimensioned to allow the heater 1005 to penetrate into the cavity of the sliding receptacle 1013.

The extractor 1001 engages with an inner portion 1025 of the device 1000 such that it may be coupled to the device 1000 in a first position and a second position, and at intermediate positions between the first position and the second position.

FIGS. 10 and 11 illustrate the extractor 1001 in its first position relative to the device 1000. In this first position the extractor 1001 abuts the first housing portion 1002. The heater 1005 penetrates into the cavity of the sliding receptacle 1013. When the extractor 1001 is in its first position, a smoking article 1111 may be inserted into the cavity of the sliding receptacle 1013 and positioned such that the heater 1005 penetrates into the aerosol-forming substrate of the smoking article. The device 1000 may then be operated to heat the aerosol-forming substrate, thereby generating an aerosol which may be inhaled by a user puffing on a mouthpiece filter 1131 of the smoking article 1111.

After the smoking article has been used, the user will wish to remove the smoking article 1111 from the device 1000. If a user pulls on the end of the smoking article nearest the mouthpiece filter 1131, portions of the aerosol-forming substrate may become dislodged from the smoking article and retained within the device. In order to remove the smoking article, therefore, a user moves the extractor from its first position to its second position, as illustrated in FIG. 12. The end wall 1014 of the sliding receptacle engages with the smoking article and helps move the aerosol-forming substrate 1030 away from the heater 1005. In the second position, the extractor has moved the smoking article entirely out of contact with the heater 1005. The smoking article 1111 may now be removed from the sliding receptacle and the extractor 1001 may be moved back to its first position.

Figure 13:
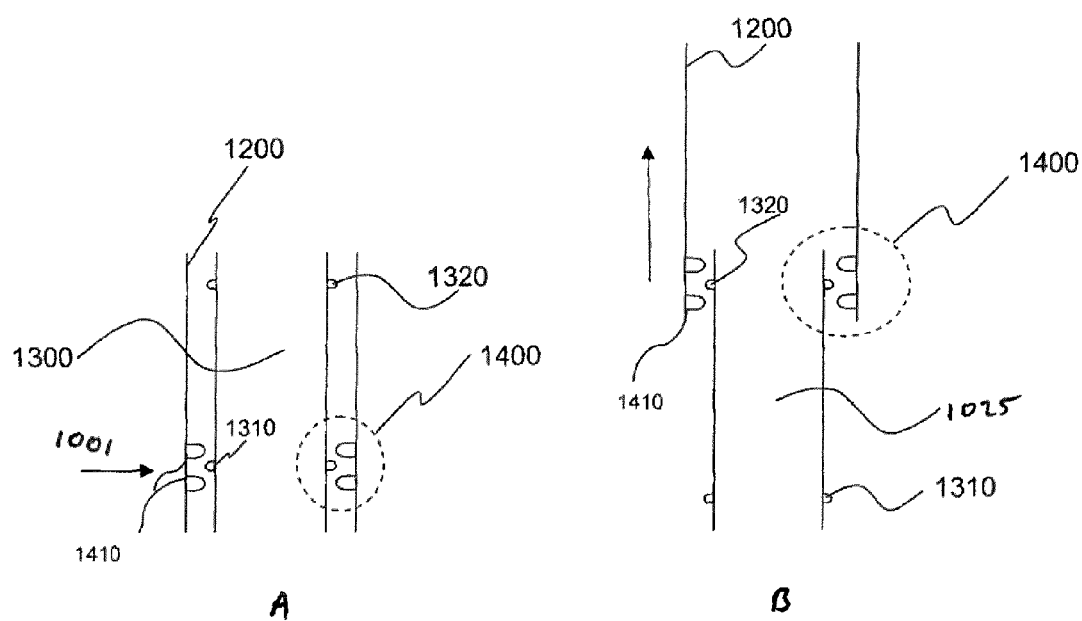
FIGS. 13A and 13B are schematic diagrams illustrating the use of snaps retain the extractor on the device of FIG. 10.

Any suitable means may be used to engage the extractor 1001 with the inner portion 1025 of the device 1000 such that it is slidable between the first position and the second position. A preferred means may involve the use of snaps, as described below with reference to FIGS. 13A and 13B.

An inner surface 1200 of the extractor 1001 engages with an outer surface of the inner portion 1025 of the device 1000. The extractor 1001 is retained on the device 1000 by means of snaps 1400 (see regions outlined by circles in FIG. 13). The snaps 1400 comprise a combination of protrusions 1410 located on an inner surface of the extractor with sprung protrusions 1310 or 1320 located on an outer surface of the inner portion 1025 of the device 1000. The inner surface 1200 of extractor has four pairs of longitudinally spaced protrusions 1410 that are circumferentially spaced within the inner surface 1200. These pairs of protrusions 1410 engage with the sprung protrusions 1310, 1320. When the extractor 1001 abuts the first housing portion 1002, the pairs of protrusions 1410 engage with a first set of sprung protrusions 1310. The extractor 1001 is thereby retained in its first position.

By applying a force in a longitudinal direction, snaps 1400 are disengaged when the protrusions 1410 on the extractor 1001 disengage with the first set of sprung protrusions 1310 and the extractor may freely slide in a longitudinal axis. To retain the extractor in its second position, longitudinally spaced from the first position, the protrusions 1410 may engage with the second sprung protrusions 1320 and snaps 1400 are reengaged with the combination of protrusions 1410 and 1320. The second sprung protrusions 1320 are longitudinally spaced from the first sprung protrusions 1310. The sprung protrusions 1310, 1320 may be sprung by cantilever springs.

The extractor 1001 may be entirely removed from the device 1000.

The invention claimed is:

1. An aerosol-generating device configured to receive an aerosol-forming substrate, the device comprising:
   a heater configured to heat the aerosol-forming substrate and configured to penetrate an internal portion of the aerosol-forming substrate; and
   an extractor configured to extract the aerosol-forming substrate received in the aerosol-generating device,
   wherein the extractor is movably coupled to the aerosol-generating device between a first position and a second position,
      the first position being an operating position defined by the heater being in contact with the aerosol-forming substrate, and
      the second position being an extraction position defined by the aerosol-forming substrate being separated from the heater, and
   wherein the extractor remains coupled to the aerosol-generating device in both the first position and the second position.

2. The device according to claim 1, wherein the extractor comprises a sliding receptacle configured to receive the aerosol-generating device, an aperture being defined through a wall of the sliding receptacle and being configured to allow the heater to penetrate the aerosol-forming substrate received within the sliding receptacle when the extractor is in the first position.

3. The device according to claim 2, further comprising a sleeve configured to receive the sliding receptacle, such that the sliding receptacle is configured to slide in the sleeve between the first and second positions.

4. The device according to claim 3, wherein the sliding receptacle includes a flange arranged to abut the sleeve.

5. The device according to claim 2, further comprising a stopper configured to prevent the sliding receptacle from sliding out of the device.

6. The device according to claim 2, further comprising a guide pin configured to guide the sliding receptacle as the sliding receptacle is moved between the first and second positions.

7. The device according to claim 2, wherein the aerosol-forming substrate is provided in a smoking article, and the sliding receptacle is in the first position when the smoking article is received in the extractor.

8. The device according to claim 2, wherein a support configured to support the aerosol-forming substrate comprises a face of the sliding receptacle, the face including at least one aperture for allowing through-flow of air.

9. The device according to claim 2, wherein the sliding receptacle comprises a grip configured to grip the aerosol-forming substrate when the aerosol-forming substrate is received in the sliding receptacle and the sliding receptacle is in the first position.

10. The device according to claim 2, wherein the sliding receptacle comprises a face against which the aerosol-forming substrate abuts when the aerosol-forming substrate is positioned so as to be heated by the heater.

11. The aerosol-generating device according to claim 1, wherein the extractor is an aerosol-forming substrate extractor configured to remove the aerosol-forming substrate from the aerosol-generating device, the aerosol-forming substrate extractor being configured to removably couple to the aerosol-generating device and comprising a sliding receptacle configured to receive the aerosol-forming substrate, an aperture being defined through a first wall of the receptacle such that the first wall is configured to engage with the aerosol-forming substrate while allowing the heater of the aerosol-generating device to penetrate the receptacle and contact the aerosol-forming substrate.

12. A method for extracting a smoking article including an aerosol-forming substrate from a heated aerosol-generating device, the heated aerosol-generating device comprising a heater configured to heat the aerosol-forming substrate to form an aerosol, and an extractor being coupled to the aerosol-generating device and comprising a sliding receptacle for receiving the smoking article, the method comprising:
   sliding the sliding receptacle, with the smoking article received in the sliding receptacle, from a first position in which the aerosol-forming substrate of the smoking article is positioned so as to be heated by the heater, to a second position in which the aerosol-forming substrate of the smoking article is substantially separated from the heater, the aerosol-forming substrate of the smoking article being supported during the sliding by a support on the sliding receptacle, the extractor remaining coupled to the aerosol-generating device in both first and second positions; and
   removing the smoking article from the sliding receptacle.

13. The method according to claim 12, in which the heated aerosol-generating system is an electrically heated aerosol-generating system comprising an electric heater.

14. The method according to claim 12, in which the smoking article comprises tobacco.

* * * * *